United States Patent [19]

Kameyama et al.

[11] 4,225,733

[45] Sep. 30, 1980

[54] METHOD FOR HYDROGENATING AN AROMATIC COMPOUND

[75] Inventors: Tetsuya Kameyama, Koganei; Masayuki Dokiya, Tokyo; Kenzo Fukuda, Niiza, all of Japan

[73] Assignee: Agency of Industrial Science & Technology, Tokyo, Japan

[21] Appl. No.: 919,985

[22] Filed: Jun. 28, 1978

[30] Foreign Application Priority Data

Jul. 7, 1977 [JP] Japan ................................. 52/81155

[51] Int. Cl.$^2$ .............................................. C07C 5/10

[52] U.S. Cl. ..................................... 585/269; 585/266; 585/272; 585/273

[58] Field of Search ......................................... 260/667

[56] References Cited

U.S. PATENT DOCUMENTS 3,344,200   9/1967   Wald et al. ........................... 260/667

*Primary Examiner*—Veronica O'Keefe
*Attorney, Agent, or Firm*—Armstrong, Nikaido, Marmelstein & Kubovcik

[57] ABSTRACT

Provided is a method for hydrogenating an aromatic compound by reacting the aromatic compound with hydrogen iodide in the presence of ruthenium catalyst.

6 Claims, No Drawings

METHOD FOR HYDROGENATING AN AROMATIC COMPOUND

BACKGROUND OF THE INVENTION

The present invention relates to a method for hydrogenating an aromatic compound.

Heretofore, there have been proposed many methods for the hydrogenation of aromatics. One of the most conventional methods is a catalytic reduction method using hydrogen gas. Such conventional method has disadvantages in economy and easiness to handle, and others.

Meanwhile, there has been known that in the case of producing hydrogen by using water and hydrogen sulfide as the raw material, iodine is used as a hydrogen acceptor and thereby hydrogen is recovered as hydrogen iodide (for example, $H_2S + I_2 \rightarrow 2HI + S$, $2H_2O + 2I_2 \rightarrow 4HI + O_2$). In such method, it is very important that hydrogen is efficiently isolated and recovered from the obtained hydrogen iodide.

SUMMARY OF THE INVENTION

The present inventors have tried to establish a method for producing hydrogen from hydrogen iodide and found an effective method in which hydrogen iodide is reacted with an aromatic compound at first and the obtained hydrogenated compound is dehydrogenated.

An object of the present invention is to provide a novel method for hydrogenating an aromatic compound at a high yield close to the theoretical yield.

Other objects and advantages of the present invention will become clearer from considering the following description.

DESCRIPTION OF PREFERRED EMBODIMENTS

According to the present invention the objects are achieved by a method for hydrogenating an aromatic compound, which comprises reacting the aromatic compound with hydrogen iodide in the presence of ruthenium catalyst.

A novel catalyst used in the method of the present invention is ruthenium catalyst. Ruthenium may be used in any form, for example, ruthenium metal, its hydroxide, its oxide or its salt of organic acid or inorganic acid. The ruthenium catalyst may also be used together with a carrier, for example, barium sulfate, alumina, silica or aluminosilicate.

Preparation of the catalyst may be easily carried out by a known method for preparing a catalyst of a metal like platinum, and generally no particular operation is required upon preparation.

As a raw material aromatic compound whatever aromatic compound capable of being subjected to a conventional hydrogenation reaction may be used. In other words, any compounds having one or more benzene nucleus may be used. Usually, an aromatic compound having 6 to 16 carbon atoms may be preferably used. Typical examples of the aromatic compound include aromatic hydrocarbons such as benzene, toluene, xylene, trimethyl benzene, tetramethyl benzene, ethyl benzene, propyl benzene, diphenyl methane, naphthalene, methyl naphthalene, of which benzene and alkyl bnezene are especially preferable. An aromatic compound having one or more substituents inert to the hydrogenation reaction, such as hydroxy group or alkoxy group, may also be used.

In the method of the present invention, the reaction temperature is preferably 25°–300° C., more preferably 25°–200° C., the reaction pressure is preferably 1–200 kg/cm², more preferably 5–100 kg/cm², and the amount of hydrogen iodide to the aromatic compound is preferably 3–20 times by mole, more preferably 6–10 times by mole.

The reaction of the present invention is preferably carried out in the presence of water. Coexistence of water brings hydrogen iodide to an aqueous layer and therefore make it easy to contact with the aromatic compound. The amount of water to hydrogen iodide is preferably 1–10 times by mole, more preferably 2–6 times by mole.

According to the present invention, the aromatic compound may be converted to the corresponding alicyclic compound at a high yield close to the theoretical yield.

On the contrary, in the case of using nickel or platinum catalyst, which is a typical catalyst in the conventional catalytic reduction in place of ruthenium catalyst in the method of the present invention, the expected results cannot be achieved.

The present invention will now be explained in greater detail in conjunction with specific examples thereof.

EXAMPLE 1

Into an autoclave having an internal capacity of about 100 ml, 40 ml (HI: $3.03 \times 10^{-1}$ mole) of an aqueous solution of hydrogen iodide (HI content being 57%, specific gravity being 1.7), 4.4 ml ($4.95 \times 10^{-2}$ mole) of benzene and 0.66 g of ruthenium hydroxide as a catalyst were charged, and a reaction was carried out under the conditions of 150° C. and 10 kg/cm² for 2 hours by stirring. The yield of the produced cyclohexane to the used benzene was 100%.

EXAMPLE 2

Using 1 g of ruthenium supported on barium sulfate (ruthenium content 5% by weight), in place of ruthenium hydroxide in example 1, a reaction was carried out under the same conditions as in example 1, and the yield found of cyclohexane was 100%.

REFERENCTIAL TEST 1

Using platinum net as a catalyst and a reaction temperature of 200° C., a reaction was carried out under the same conditions as in example 1, and the yield found of cyclohexane was only 5%.

What is claimed is:

1. A method of hydrogenating an aromatic compound comprising: contacting an aromatic compound selected from the group consisting of benzene and alkyl benzene having 1 to 3 alkyl substituents at a temperature of from 25° to 300° C. under a reaction pressure within a range of 1–200 kg/cm², with a catalytic amount of a catalyst selected from the group consisting of metal ruthenium, ruthenium hydroxide, ruthenium oxide and a ruthenium salt of an organic acid or inorganic acid, said catalyst being unsupported or supported on a carrier selected from the group consisting of barium sulfate and alumina, and a reducing agent consisting of hydrogen iodide, the amount of the hydrogen iodide being 3–20 times the amount of the aromatic compound, by mole, to completely hydrogenate the aromatic compound and produce an alicyclic compound corresponding to the aromatic compound in near theoretical yields and recovering the alicyclic compound.

2. The method according to claim 1, in which the hydrogenation reaction is carried out in the presence of water.

3. The method according to claim 2, in which the amount of water to hydrogen iodide is 1-10 times by mole.

4. The method according to claim 1 in which a catalytic amount of metal ruthenium is used.

5. The method according to claim 1 in which a catalytic amount of ruthenium hydroxide is used.

6. The method according to claim 1 in which a catalytic amount of ruthenium oxide is used.

* * * * *